United States Patent
Okada (10) Patent No.: US 9,339,168 B2
(45) Date of Patent: May 17, 2016

(54) ENDOSCOPE OPERATION PORTION STRUCTURE

(71) Applicant: OLYMPUS CORPORATION, Tokyo (JP)

(72) Inventor: Takeshi Okada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 54 days.

(21) Appl. No.: 14/328,830

(22) Filed: Jul. 11, 2014

(65) Prior Publication Data

US 2014/0359972 A1 Dec. 11, 2014

Related U.S. Application Data

(63) Continuation of application No. PCT/JP2013/076036, filed on Sep. 26, 2013.

(30) Foreign Application Priority Data

Feb. 7, 2013 (JP) ................................. 2013-022457

(51) Int. Cl.
*A61B 1/04* (2006.01)
*A61B 1/00* (2006.01)
*G02B 23/24* (2006.01)

(52) U.S. Cl.
CPC ........... *A61B 1/00066* (2013.01); *A61B 1/0011* (2013.01); *G02B 23/24* (2013.01); *G02B 23/2476* (2013.01); *Y10T 16/14* (2015.01)

(58) Field of Classification Search
CPC .. A61B 1/00066; A61B 1/0011; G02B 23/24; G02B 23/2476; Y10T 16/44
See application file for complete search history.

(56) References Cited

U.S. PATENT DOCUMENTS

| 3,468,565 | A | * | 9/1969 | Roder | B60K 26/00 285/194 |
| 3,796,870 | A | * | 3/1974 | Pettyjohn, Jr. | F21S 8/02 362/223 |
| 4,488,701 | A | * | 12/1984 | Leigh-Monstevens | B60T 11/16 248/637 |
| 4,552,129 | A | * | 11/1985 | Utsugi | A61B 1/00137 600/131 |
| 4,640,478 | A | * | 2/1987 | Leigh-Monstevens | B60T 11/16 248/27.1 |
| 5,082,462 | A | * | 1/1992 | Oswald, Jr. | H01R 13/111 439/380 |

(Continued)

FOREIGN PATENT DOCUMENTS

| JP | 07-051218 A | 2/1995 |
| JP | 08-036137 A | 2/1996 |

(Continued)

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

An endoscope operation portion structure includes: a frame member inserted from an opening portion on an operation portion main body and arranged; a first fixing portion formed such that a length between a first apex protruded from one side of the frame member and a point on another side opposed to the first apex is longer than a long side of the opening portion; and a second fixing portion formed such that a length between a second apex protruded from the other side of the frame member and a point on the one side opposed to the second apex is longer than the long side of the opening portion, wherein the length between the first apex and the point on the other side and the length between the second apex and the point on the one side portion are shorter than a diagonal direction of the opening portion.

5 Claims, 11 Drawing Sheets

(56) References Cited

U.S. PATENT DOCUMENTS

| | | | |
|---|---|---|---|
| 6,716,160 B2* | 4/2004 | Mitsumori | A61B 1/005 600/131 |
| 7,223,231 B2* | 5/2007 | Akiba | A61B 1/0052 600/130 |
| 2002/0054493 A1* | 5/2002 | Sei | G01J 3/02 362/373 |
| 2003/0158462 A1 | 8/2003 | Takase | |
| 2004/0077928 A1* | 4/2004 | Moriyama | A61B 1/00089 600/127 |
| 2007/0246506 A1* | 10/2007 | Hamazaki | A61B 1/0008 227/175.1 |
| 2008/0200763 A1* | 8/2008 | Ueno | A61B 1/00039 600/146 |
| 2009/0225159 A1* | 9/2009 | Schneider | A61B 1/00124 348/82 |
| 2010/0160730 A1* | 6/2010 | Konomura | G02B 23/2476 600/114 |
| 2011/0112361 A1* | 5/2011 | Ishigami | A61B 1/00052 600/109 |
| 2012/0016191 A1* | 1/2012 | Ito | A61B 1/00087 600/104 |
| 2012/0078054 A1* | 3/2012 | Ueno | A61B 1/005 600/149 |
| 2012/0253116 A1* | 10/2012 | Sniffin | A61B 18/14 600/106 |
| 2013/0034825 A1* | 2/2013 | Phillips | A61B 1/00016 433/29 |
| 2014/0142388 A1* | 5/2014 | Suzuki | A61B 1/0011 600/141 |
| 2014/0187864 A1* | 7/2014 | Kubo | A61B 1/00066 600/139 |
| 2014/0200513 A1* | 7/2014 | Koitabashi | A61B 1/00066 604/95.04 |
| 2014/0336456 A1* | 11/2014 | Demers | A61B 1/018 600/106 |
| 2014/0357954 A1* | 12/2014 | Koyama | A61B 1/0011 600/118 |

FOREIGN PATENT DOCUMENTS

| | | |
|---|---|---|
| JP | 09-164111 A | 6/1997 |
| JP | 11-192199 A | 7/1999 |
| JP | 2002186580 A | 7/2002 |
| JP | 2003-174997 A | 6/2003 |
| JP | 2013-150700 A | 8/2013 |

* cited by examiner

//ENDOSCOPE OPERATION PORTION STRUCTURE

CROSS REFERENCE TO RELATED APPLICATION

This application is a continuation application of PCT/JP2013/076036 filed on Sep. 26, 2013 and claims benefit of Japanese Application No. 2013-022457 filed in Japan on Feb. 7, 2013, the entire contents of which are incorporated herein by this reference.

BACKGROUND OF THE INVENTION

1. Field of the Invention

The present invention relates to an endoscope operation portion structure including a frame inside thereof.

2. Description of the Related Art

Endoscopes are widely known, which can be introduced from an outside to an inside of a living body or construction in order to observe a site such as the inside of the living body or construction which is difficult to be observed. Such an endoscope generally includes an insertion portion provided so as to be continuous from an operation portion, and an observation window provided at a distal end portion of the insertion portion.

Observation, treatment and the like are performed by the endoscope such that a bending portion, or the like, provided at the insertion portion is operated to be bent in the state where the operation portion is grasped and the insertion portion is inserted into a site to be observed in a subject. Therefore, the operation portion from which the insertion portion is continuously provided is required to have a sufficient strength. For example, Japanese Patent Application Laid-Open Publication No. 11-192199 discloses an endoscope including a base plate as a frame for ensuring rigidity.

The base plate recited in the Japanese Patent Application Laid-Open Publication No. 11-192199 includes a stopper at a thick wall portion. The stopper is provided in order to prevent excessive load from being applied to an operation portion casing (also referred to as operation portion main body) when a holding portion casing (also referred to as grasping portion) of the operation portion is fixed, and prevent the base plate from being drawn out in a direction of the insertion portion.

SUMMARY OF THE INVENTION

An endoscope operation portion structure according to one aspect of the present invention includes: an operation portion main body for operating an endoscope; a rectangular opening portion which is open on the operation portion main body; a frame member to be inserted from the opening portion into the operation portion main body and arranged inside the operation portion main body; a first fixing portion for fixing the frame member to the operation portion main body, the first fixing portion being provided so as to protrude from one side portion of the frame member and formed such that a length between a protruded first apex and a point on another side portion of the frame member, which is opposed to the protruded first apex, is longer than a length in a long side direction of the opening portion; and a second fixing portion for fixing the frame member to the operation portion main body, the second fixing portion being provided so as to protrude from the other side portion of the frame member and formed such that a length between a protruded second apex and a point on the one side portion, which is opposed to the protruded second apex, is longer than the length in the long side direction of the opening portion, wherein the length between the first apex and the point on the other side portion which is opposed to the first apex and the length between the second apex and the point on the one side portion which is opposed to the second apex are shorter than a length in a diagonal direction of the opening portion.

An endoscope operation portion structure according to another aspect of the present invention includes: an operation portion main body for operating an endoscope; a rectangular opening portion which is open on the operation portion main body; a frame member to be inserted from the opening portion into the operation portion main body and arranged inside the operation portion main body; a first fixing portion for fixing the frame member to the operation portion main body, the first fixing portion being formed so as to protrude from one side portion of the frame member; and a second fixing portion for fixing the frame member to the operation portion main body, the second fixing portion being formed so as to protrude from another side portion of the frame member, the second fixing portion having a second apex arranged separately from a first apex of the first fixing portion such that a length in a width direction of the frame member at the second apex is longer than a length in the long side direction of the opening portion, wherein the first fixing portion and the second fixing portion are respectively arranged at positions separated from each other by a predetermined distance in a direction of a longitudinal axis of the frame member, and a length between the first apex and a point on the other side portion which is opposed to the first apex and a length between the second apex and a point on the one side portion which is opposed to the second apex are shorter than the length in the long side direction of the opening portion.

The present invention as described above is capable of providing an endoscope operation portion structure which enables a frame member as a base plate to be fixed to an operation portion with stable strength, with reduced cost and weight by reducing the number of components and assembling man-hours.

DETAILED DESCRIPTION OF THE PREFERRED EMBODIMENT

Hereinafter, the present invention will be described with reference to drawings. Note that, in the respective drawings used in the description below, a different scale size is used for each of the components in order to allow each of the components to be illustrated in a recognizable size in the drawings, and the present invention is not limited to the number, shapes, ratio of the sizes of the components, and a relative positional relationship among the components shown in these drawings.

Figure 1:
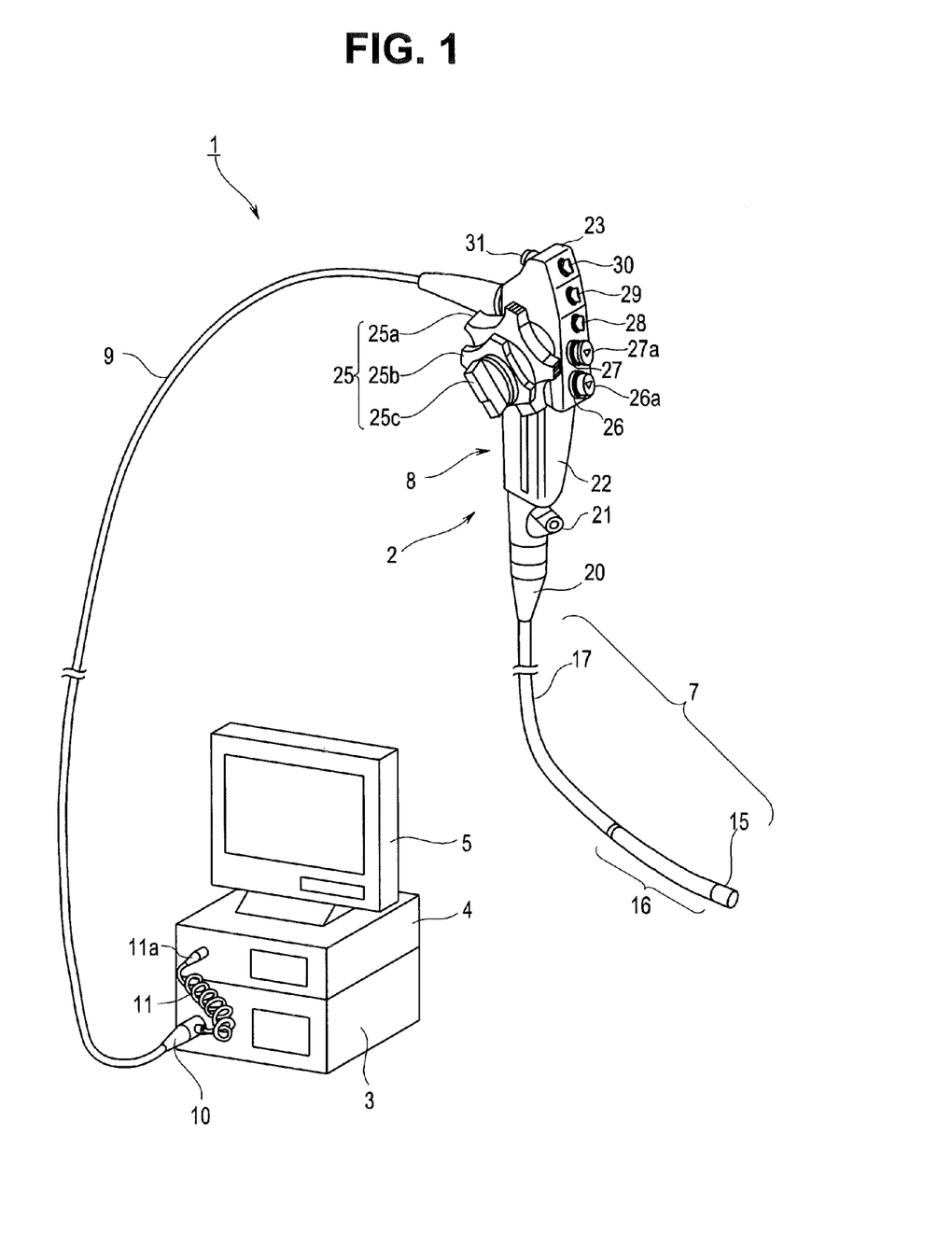
FIG. 1 illustrates a configuration of an endoscope according to one aspect of the present invention.
Figure 2:
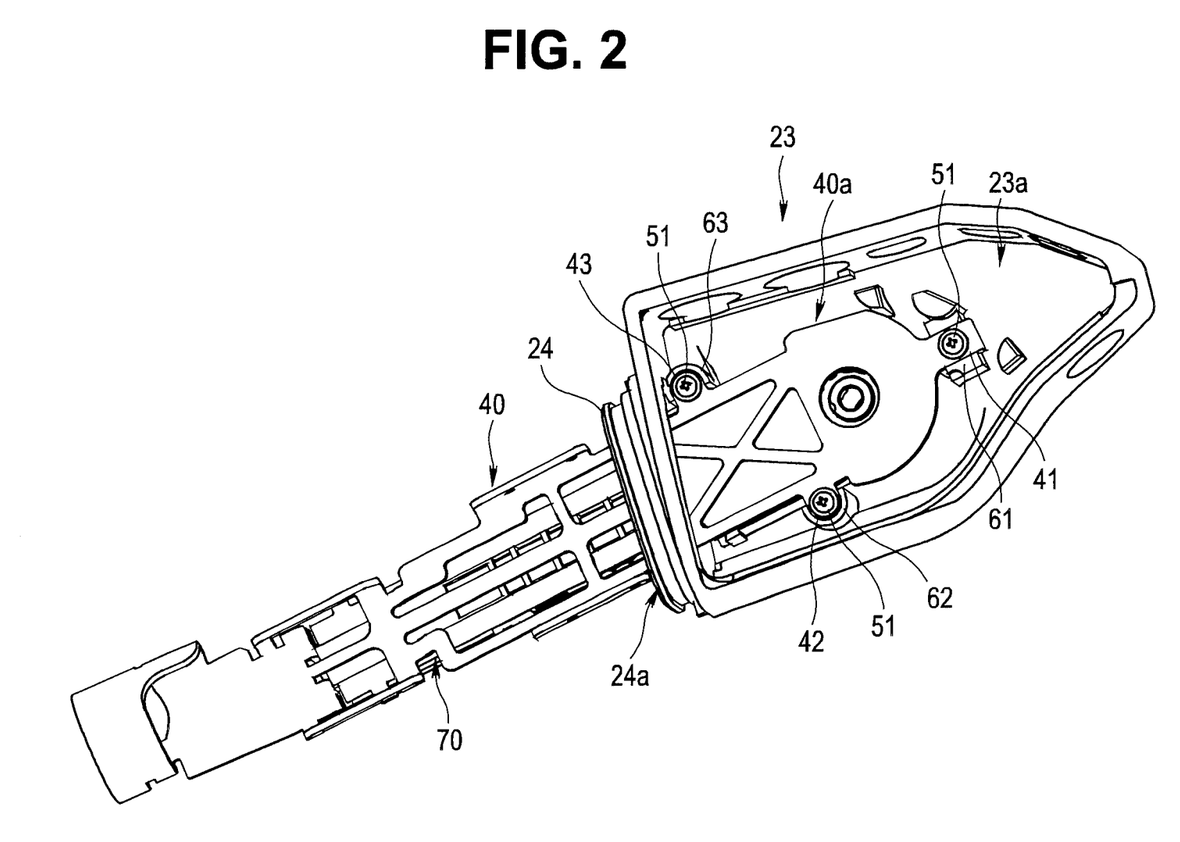
FIG. 2 is a perspective view showing a configuration in which a frame member is fixed to an operation portion main body, according to the one aspect.
Figure 3:
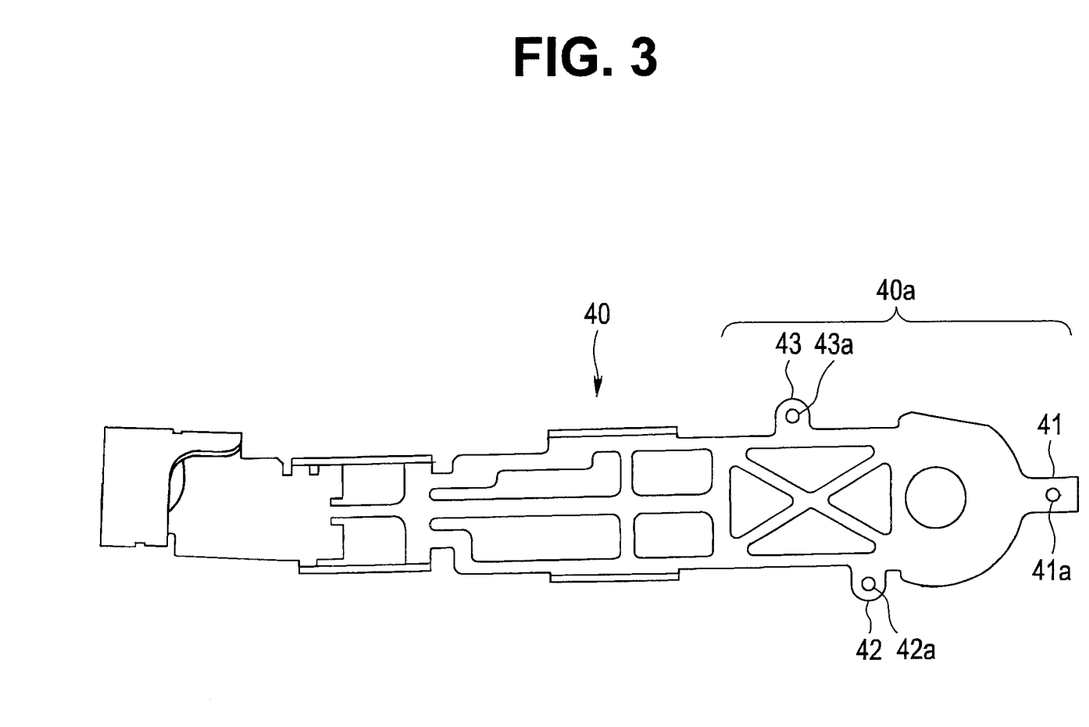
FIG. 3 is a plan view showing a configuration of the frame member according to the one aspect.
Figure 4:
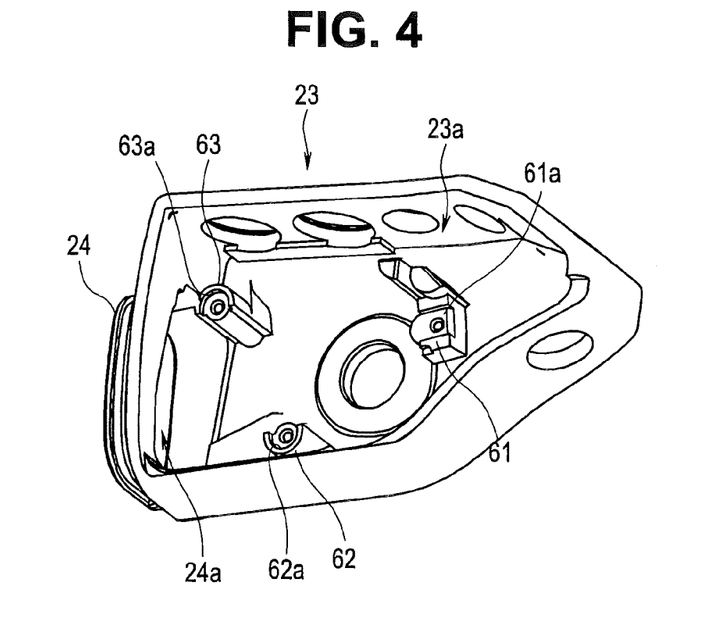
FIG. 4 is a perspective view showing a configuration of the operation portion main body according to the one aspect.
Figure 5:
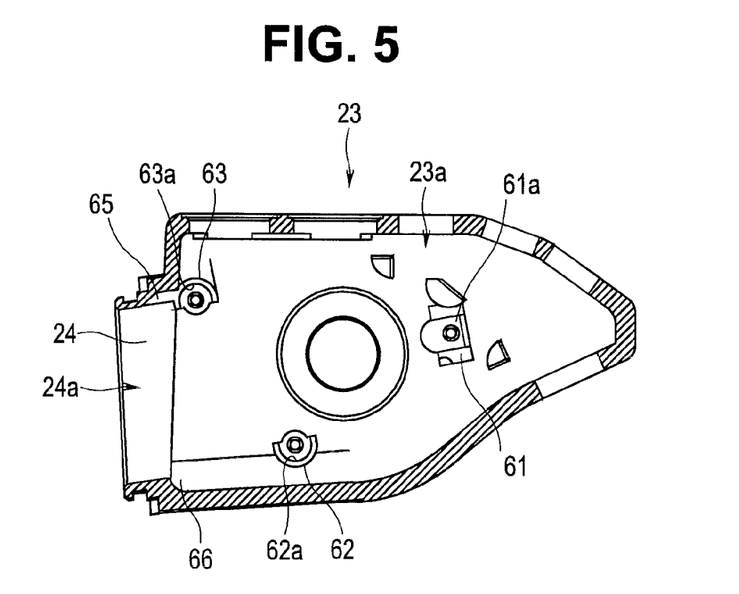
FIG. 5 is a cross-sectional view showing the configuration of the operation portion main body according to the one aspect.
Figure 6:
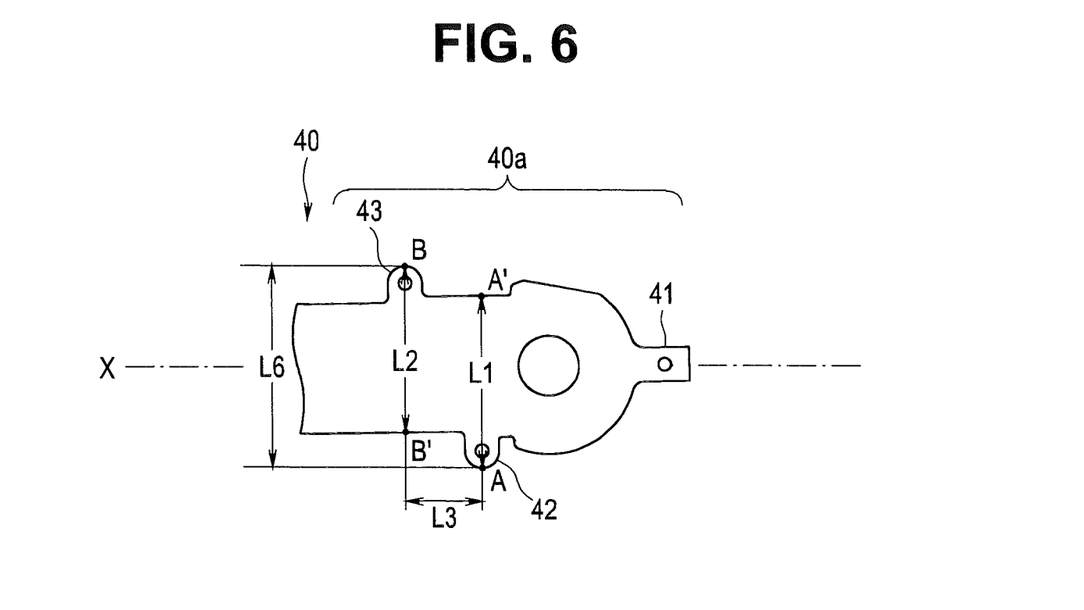
FIG. 6 is a plan view showing dimensions in a width direction of the frame member at positions of second and third screw fixing portions provided at one end part of the frame member, according to the one aspect.
Figure 7:
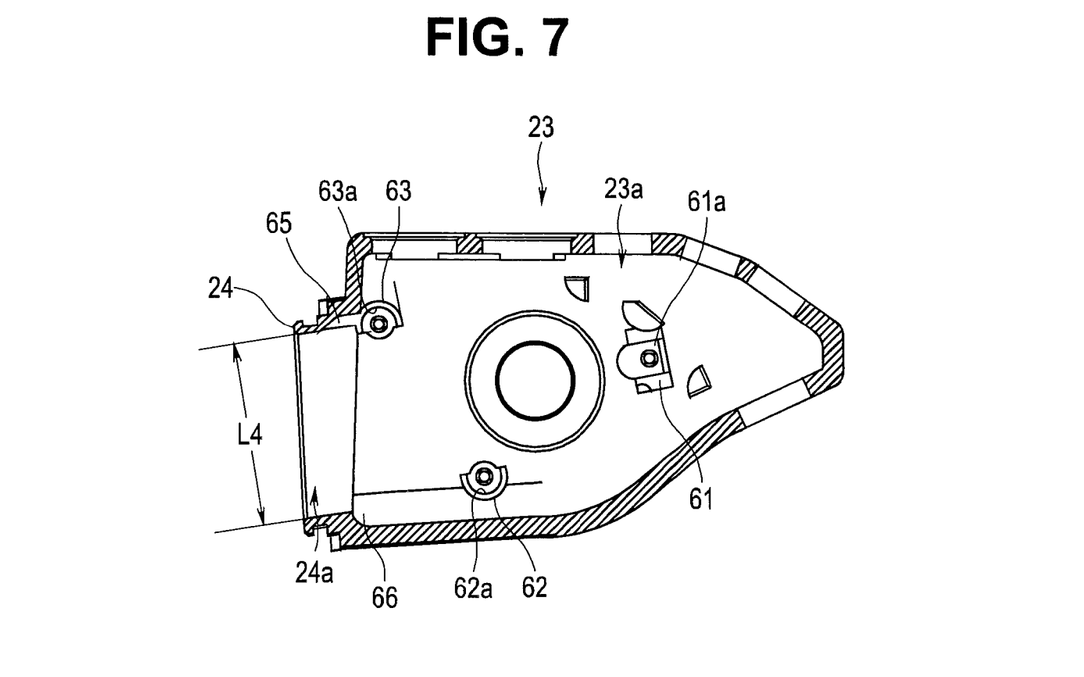
FIG. 7 is a cross-sectional view showing a length dimension in a long side direction of an opening portion provided at a coupling portion of the operation portion main body, according to the one aspect.
Figure 8:
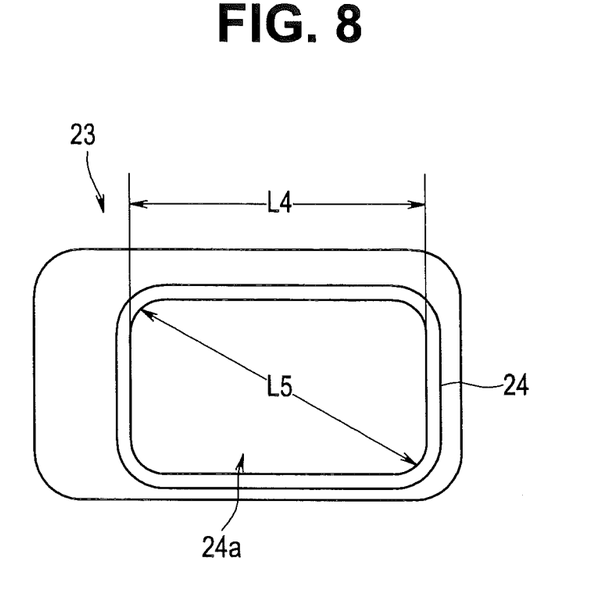
FIG. 8 is a front view showing length dimensions in the long side direction and a diagonal direction of the opening portion provided at the coupling portion of the operation portion main body, according to the one aspect.
Figure 13:
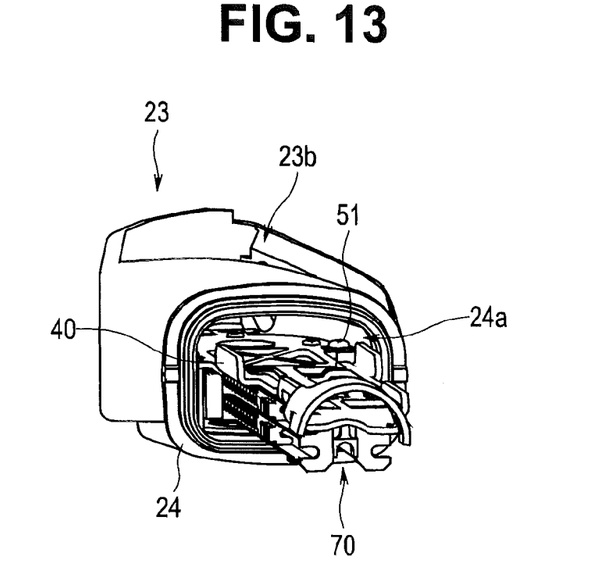
FIG. 13 is a perspective view showing a state where the frame member is fixed to the operation portion main body, according to the one aspect.
Figure 14:
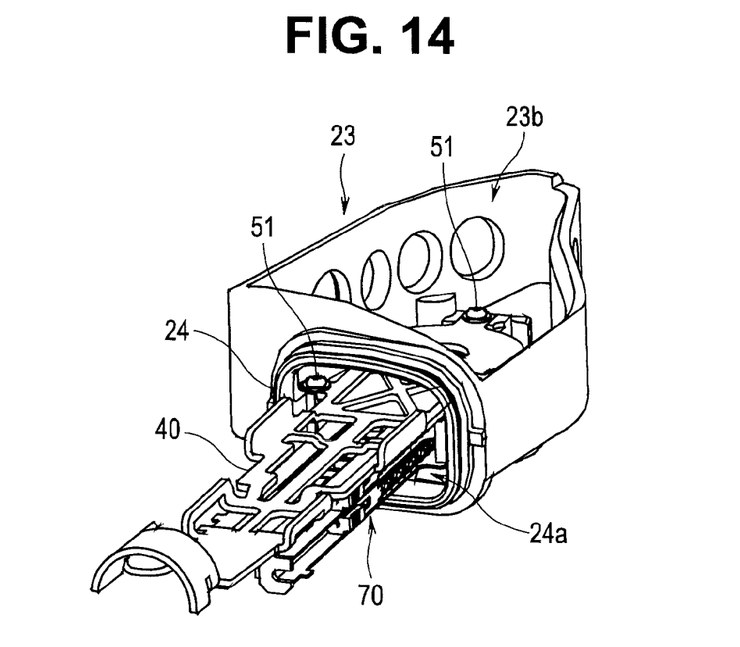
FIG. 14 is a perspective view showing the state where the frame member is fixed to the operation portion main body, according to the one aspect.

Hereinafter, an embodiment of the present invention will be described with reference to the drawings. Drawings relate to one embodiment of the present invention. FIG. 1 illustrates an endoscope system, FIG. 2 is a perspective view showing a configuration in which a frame member is fixed to an operation portion main body, FIG. 3 is a plan view showing a configuration of the frame member, FIG. 4 is a perspective view showing a configuration of the operation portion main body, FIG. 5 is a cross-sectional view showing the configuration of the operation portion main body, FIG. 6 is a plan view showing dimensions in a width direction of the frame member at positions of second and third screw fixing portions provided at one end part of the frame member, FIG. 7 is a cross-sectional view showing a length dimension in a long side direction of an opening portion provided at a coupling portion of the operation portion main body, FIG. 8 is a front view showing length dimensions in the long side direction and a diagonal direction of the opening portion provided at the coupling portion of the operation portion main body, FIGS. 9 to 12 show a state where the frame member is inserted into the operation portion main body, and FIGS. 13 and 14 are perspective views showing a state where the frame member is fixed to the operation portion main body.

As shown in FIG. 1, a main portion of an endoscope system 1 according to the present embodiment is constituted of an endoscope 2, a light source apparatus 3, a video processor 4 as a CCU (camera control unit), and a monitor 5.

As shown in FIG. 1, the endoscope 2 includes: an insertion portion 7 as an elongated hollow long member to be inserted into an observation target site; an operation portion 8 provided in a linked manner at a proximal end portion of the insertion portion 7; a universal cable 9 provided so as to be extended from a side surface portion of the operation portion 8; a light source connector 10 provided at an extension end portion of the universal cable 9; an electric cable 11 extended from a side portion of the light source connector 10; and an electric connector 11a disposed at an extension end of the electric cable 11. Note that the light source connector 10 is detachably connected to the light source apparatus 3, and the electric connector 11a is detachably connected to the video processor 4.

The insertion portion 7 includes at a distal end side thereof a distal end portion 15, and a bending portion 16, which is a bendable movable portion, provided in a linked manner at a proximal end portion of the distal end portion 15. Furthermore, a flexible tube portion 17 having long length and flexibility, which is made of a soft tubular member and provided in a linked manner at a proximal end portion of the bending portion 16.

The operation portion 8 includes a bend preventing portion 20 connected to the proximal end side of the insertion portion 7, a treatment instrument insertion port 21 which is disposed in the vicinity of the bend preventing portion 20 and communicates with a treatment instrument insertion channel in the insertion portion 7, a grasping portion 22 disposed on the side closer to the base portion than the treatment instrument insertion port 21, and an operation portion main body 23 provided in a linked manner on the proximal end side of the grasping portion 22.

The operation portion main body 23 is provided with a bending operation knob 25 for operating the bending portion 16 of the insertion portion 7. The bending operation knob 25 includes a UD bending operation knob 25a for bending the bending portion 16 in up and down directions and an RL bending operation knob 25b for bending the bending portion 16 in right and left directions, and the UD bending operation knob and the RL bending operation knob are arranged in a superimposed manner so as to be coaxially rotatable. Furthermore, a release knob 25c, which is operated to stop/release the rotational movement of the respective bending operation knobs 25a, 25b, is provided at the center portion of the RL bending operation knob 25b.

Furthermore, the operation portion main body 23 is provided with an air/water feeding cylinder 26 which communicates with a water feeding tank (not shown), a suction cylinder 27 which communicates with a suction tank (not shown), and four pressing switch devices (remote switches) 28, 29, 30 and 31, for example. A detachable air/water feeding button 26a is fitted to the air/water feeding cylinder 26. A detachable suction button 27a is fitted to the suction cylinder 27. In addition, the respective switch devices 28, 29, 30 and 31 are assigned with an image freeze function for making an endoscopic image stand still, a function for transmitting image data to a printer, various functions for adjusting an endoscopic image, and the like, appropriately.

As shown in FIG. 1, for example, the air/water feeding cylinder 26, the suction cylinder 27, and the three switch devices 28, 29 and 30 are arranged on a line along the direction of the longitudinal axis of the operation portion 8 on one side surface portion which is a side where the treatment instrument insertion port 21 is open. In addition, the one remaining switch device 31 is arranged on another side surface (side surface portion which is opposite side of the one side surface portion) which is a side where the universal cable 9 is extended.

The light source apparatus 3 supplies illumination light to a light guide, not shown, provided in the endoscope 2. That is, inside the universal cable 9, operation portion 8 and insertion portion 7 of the endoscope 2 according to the present embodiment, the light guide, not shown, is disposed, and the light source apparatus 3 supplies illumination light, via the light guide, to an illumination optical system (not shown) which configures an illumination window of the distal end portion 15. A site of the subject is irradiated with the illumination light through the illumination optical system. Note that the light source apparatus 3 is attached with the above-described water feeding tank, and incorporates a water feeding pump (not shown) that feeds sterilized water from the water feeding tank to the endoscope 2.

The video processor 4 converts data of the image picked up by the endoscope 2 into a video signal as appropriate, based on operation signals from the switch devices 28 to 31, for example, and causes the monitor 5 to display the video signal.

When using the endoscope system 1 thus configured, an operator such as a surgeon generally grasps the insertion portion 7 with the right hand and grasps the operation portion 8 with the left hand. In this case, grasping of the operation portion 8 can be performed by the operator generally grasping the grasping portion 22 with the middle finger, the medicinal finger, and the little finger of the left hand from the side from which the universal cable 9 is extended. When grasping the operation portion 8 in this way, the operator can operate the air/water feeding button 26a, the suction button 27a and the switch devices 28, 29 and 30 mainly with the index finger of the left hand, and can operate the switch device 31 with the thumb. At that time, the operator can perform switching operation of the switch devices 28, 29 and 30 which are located far from the grasping portion 22, not only with pressing operation from the vertical direction but also with the pressing operation from the horizontal direction.

Here, as the endoscope operation portion structure according to the present embodiment, description will be made on the configurations of the operation portion main body 23 of the operation portion 8 and the frame member 40 as a base plate fixed to the operation portion main body 23.

As shown in FIGS. 2 and 3, the frame member 40 is provided in the operation portion 8, and one end part 40a, which is the proximal end side, is inserted in the operation portion main body 23 to be fixed at three positions with three fixing screws 51 as fixing members. The frame member 40 is a metal frame or a rigid resin frame formed by plating or die-casting, and three screw fixing portions, i.e., first, second and third screw fixing portions 41, 42 and 43 are provided at the one end part 40a to be inserted into the operation portion main body 23.

The first screw fixing portion 41 is a convex portion protruded from the one end part 40a toward the proximal end side along the longitudinal direction of the frame member 40. The first screw fixing portion 41 has a rectangular shape in which a screw hole 41a is formed, and the end portion in the protruding direction is folded to form an L-shaped cross section.

The second screw fixing portion 42 is a convex portion protruded from one side portion of the frame member 40 in one direction perpendicular to the longitudinal direction. The second screw fixing portion 42 has an arc-shaped protruded end part in which a screw hole 42a is formed.

The third screw fixing portion 43 is a convex portion protruded from another side portion of the frame member 40 in another direction which is perpendicular to the longitudinal direction and which is opposite to the direction in which the second screw fixing portion 42 is protruded. The third screw fixing portion 43 also has an arc-shaped protruded end part in which a screw hole 43a is formed.

The second screw fixing portion 42 is disposed at a position on the side portion of the frame member 40, which is different from the side portion where the third fixing portion is disposed, so as to be located near to the first screw fixing portion 41 relative to the third screw fixing portion 43. That is, the second screw fixing portion 42 and the third screw fixing portion 43 configure two convex portions which are formed on both side portions perpendicular to the longitudinal direction of the frame member 40 and protruded respectively from the different side portions of the frame member 40 in the directions away from the frame member so as to be located at staggered positions separated from each other by a predetermined distance.

As shown in FIGS. 4 and 5, the operation portion main body 23 is a case body having an opening portion 24a formed on one side surface portion. A plate-shaped cover body, not shown, is attached to the opening portion 23a to cover the opening portion. In addition, the operation portion main body 23 has a coupling portion 24 coupled with the grasping portion 22 (see FIG. 1). The coupling portion 24 is provided with an O-ring (not shown) for maintaining water-tightness with respect to the grasping portion 22. Note that the coupling portion 24 has an opening portion 24a into which the one end part 40a of the frame member 40 is inserted.

Inside the operation portion main body 23, first, second and third screw receiving portions 61, 62 and 63 with which the three screw fixing portions, i.e., the first, second and third screw fixing portions 41, 42 and 43 of the frame member 40 are engaged and fixed. The first, second and third screw receiving portions 61, 62 and 63 include concave portions 61a, 62a and 63a with which the first, second, and third screw fixing portions 41, 42 and 43 are respectively engaged.

Note that the first screw fixing portion 41, the cross section of which is formed in an L-shape, of the frame member 40 is engaged with the first concave portion 61a of the first screw receiving portion 61 so as to be latched, and fixed to the first concave portion with the fixing screw 51. In addition, the second and third screw fixing portions 42, 43 of the frame member 40 are engaged with the concave portions 62a, 63a of the second and third screw receiving portions 62, 63, and fixed to the concave portions with the fixing screws 51 in the state where the arc-shaped side surfaces in the respective thickness directions of the second, third screw fixing portions 42, 43 contact the arc-shaped wall surfaces which form the concave portions 62a, 63a.

Furthermore, concave-shaped portions 65, 66 are formed inside the operation portion main body 23 at positions in the vicinity of the coupling portion 24 so as to prevent the second and third screw fixing portions 42, 43 from getting stuck and allow the one end part 40 to be smoothly inserted into the operation portion main body 23 in the process of inserting the one end part 40a of the frame member 40 from the opening portion 24a.

Here, description will be made on the dimensional relation between the frame member 40 and the opening portion 24a of the coupling portion 24 of the operation portion main body 23.

As shown in FIG. 6, the frame member 40 is configured such that lengths L1, L2 in the width direction perpendicular to the longitudinal axis X at the positions of the second and third screw fixing portions 42, 43 are defined as dimensions which allow the one end part 40a to be insertable into the operation portion main body 23 from the opening portion 24a of the coupling portion 24. Note that the longitudinal axis X of the frame member 40 coincides with an axis line direction of the insertion portion 7 coupled to the operation portion 8.

More specifically, the frame member 40 has the length L1 in the width direction which connects an apex A of the second screw fixing portion 42 and a point A' on the side portion which is perpendicular to the longitudinal axis X as the axis line direction of the insertion portion 7. Furthermore, the frame member 40 has the length L2 in the width direction which connects an apex B of the third screw fixing portion 43 and a point B' on the side portion which is perpendicular to the longitudinal axis X as the axis line direction of the insertion portion 7. Note that the lengths L1 and L2 are set to be substantially the same (L1≈L2). The second and third screw fixing portions 42, 43 are provided so as to protrude at positions separated from each other on both side portions of the frame member 40 in a staggered manner so as to be separated from each other by a length L3 in the direction of the longitudinal axis X.

The opening portion 24a of the coupling portion 24 of the operation portion main body 23 is a rectangular hole portion having a length L4 in the long side direction and a length L5 in the diagonal direction, as shown in FIG. 7 and FIG. 8. The length L4 in the long side direction of the opening portion 24a is set to be shorter than the respective lengths L1 and L2 in the width direction at the positions of the second and third screw fixing portions 42, 43 of the frame member 40 (L4<L1, L2). In addition, the length L5 in a diagonal direction of the opening portion 24a is set to be longer than the respective lengths L1 and L2 in the width direction at the positions of the second and third screw fixing portions 42, 43 of the frame member 40 (L5>L1, L2).

Figure 9:
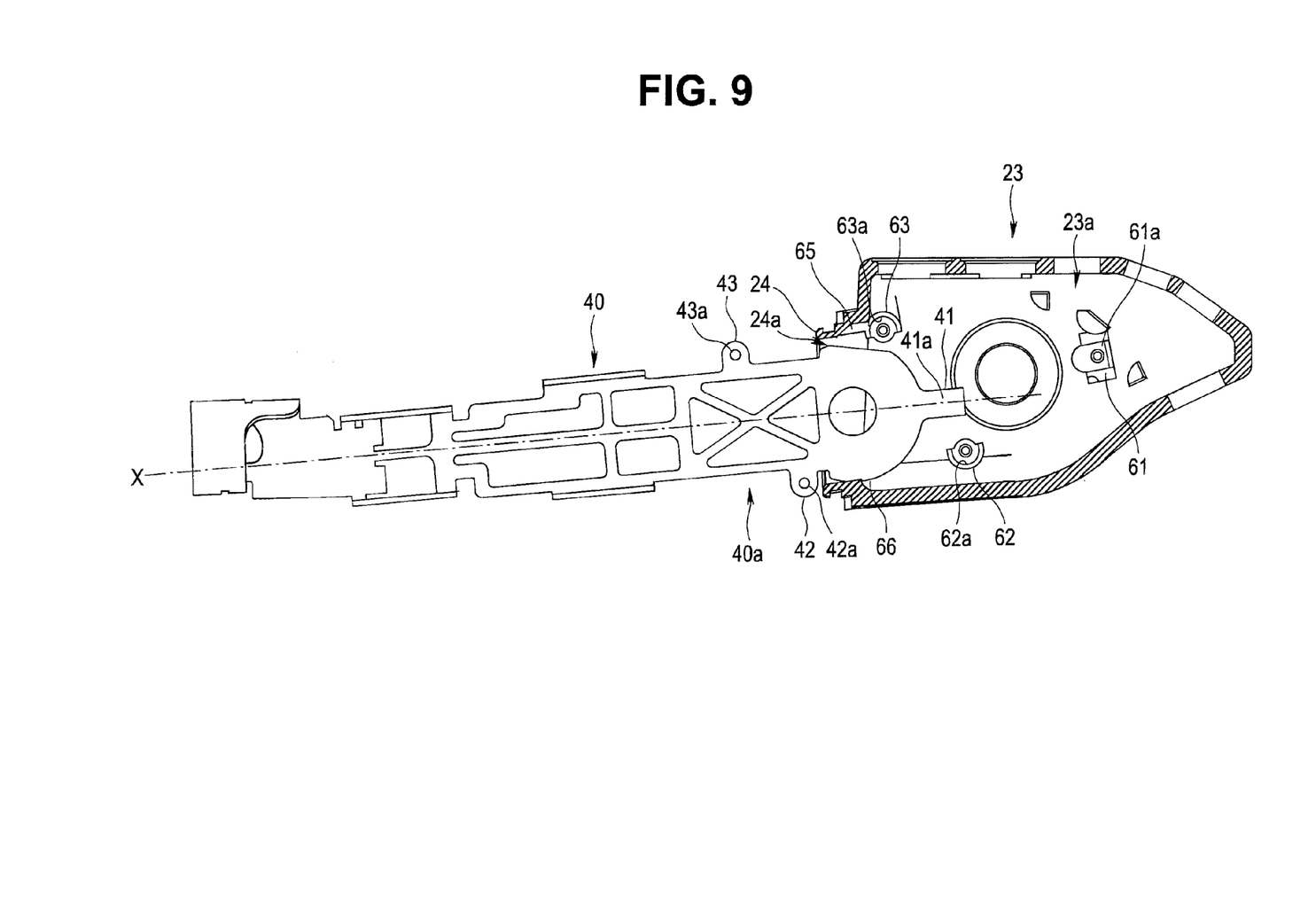
FIG. 9 illustrates a state where the frame member is inserted into the operation portion main body, according to the one aspect.

With the frame member 40 and the operation portion main body 23 which are configured as described above, when the frame member 40 is inserted into the operation portion main body 23 and fixed thereto, the frame member 40 is inserted into the opening portion 24a of the coupling portion 24 of the operation portion main body 23 from the one end part 40a side, as shown in FIG. 9. Note that the frame member 40 is fixed to the operation portion main body 23 in the state where a chain block 70 (See FIGS. 2, 13 and 14) to which bending operation wires of the bending portion 16 are connected is mounted on the frame member in advance. The chain block 70 includes a sprocket coupled to the bending operation knob 25, a chain unit configured to be geared with the sprocket to pull and relax the bending operation wires, and the like are provided. Since such a configuration is well-known, detailed description of thereof will be omitted.

Figure 10:
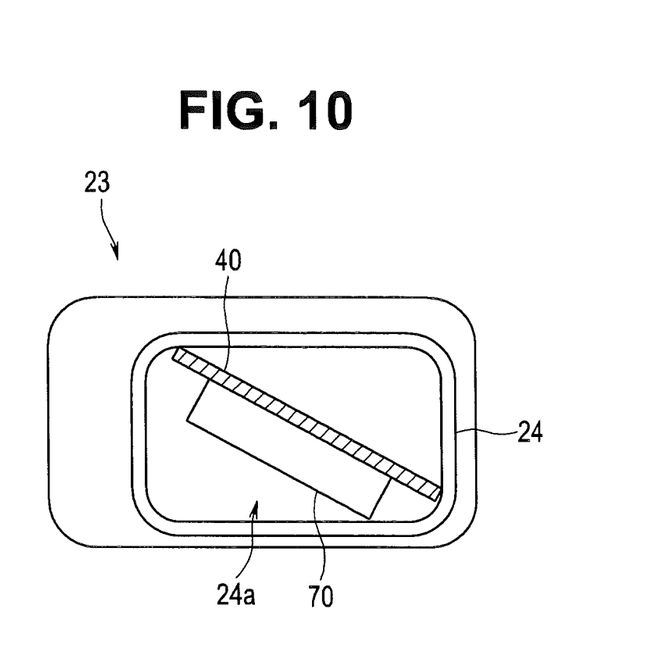
FIG. 10 illustrates the state where the frame member is inserted into the operation portion main body, according to the one aspect.

When the frame member 40 is inserted into the opening portion 24a of the coupling portion 24 of the operation portion main body 23, the frame member 40 is inserted into the opening portion 24a such that the plate surface is rotated so as to be twisted, and inclined in accordance with the diagonal direction of the opening portion 24a, as shown in FIG. 10. That is, since the frame member 40 is configured such that the lengths L1, L2 in the width direction at the positions of the second and third screw fixing portions 42, 43 are longer than the length L4 in the long side direction of the opening portion 24a of the coupling portion 24 and shorter than the length L5 in the diagonal direction of the opening portion 24a, the frame member 40 is inclined to be enabled to pass through the opening portion 24a of the coupling portion 24 and inserted into the operation portion main body 23.

Figure 11:
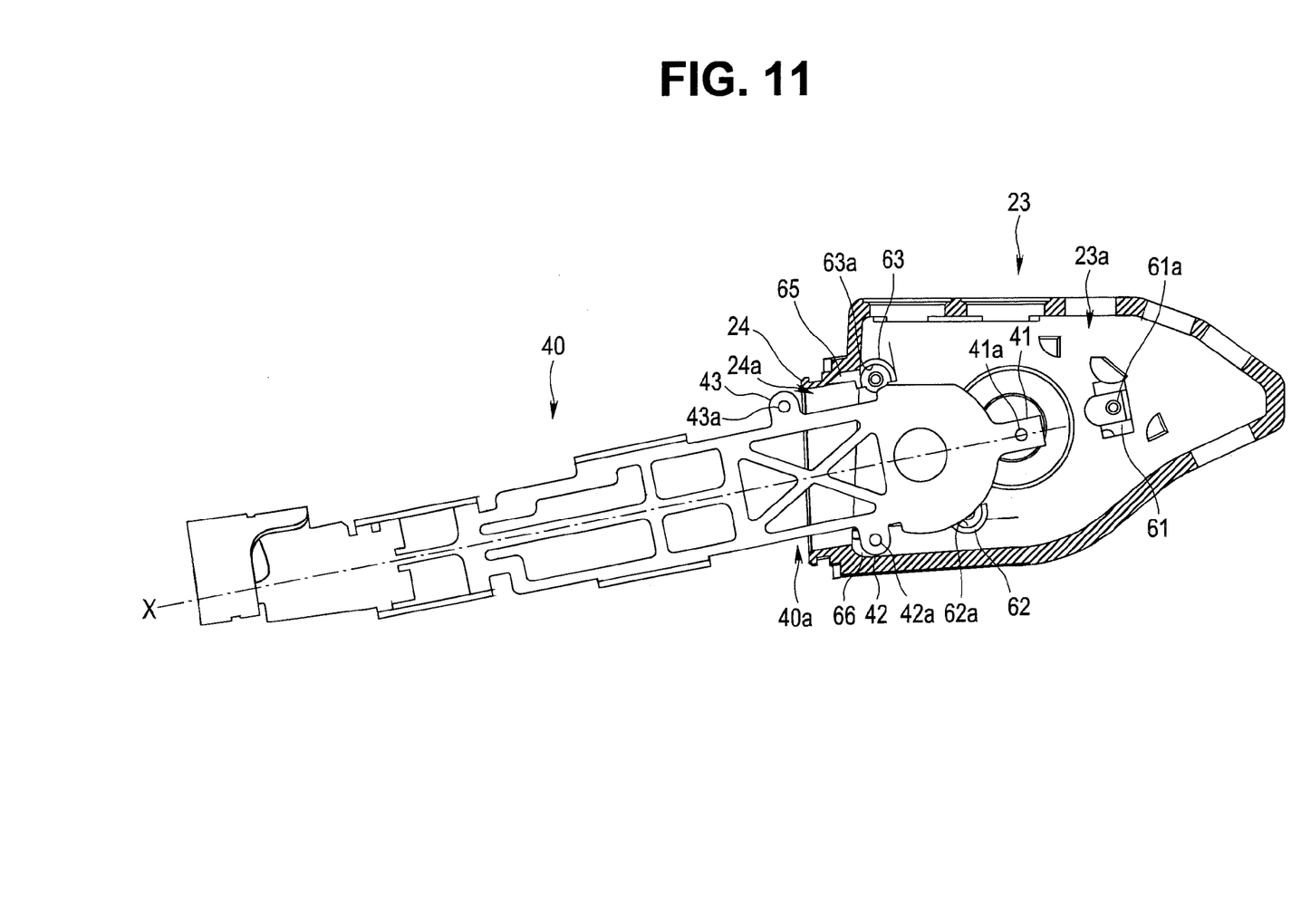
FIG. 11 illustrates the state where the frame member is inserted into the operation portion main body, according to the one aspect.
Figure 12:
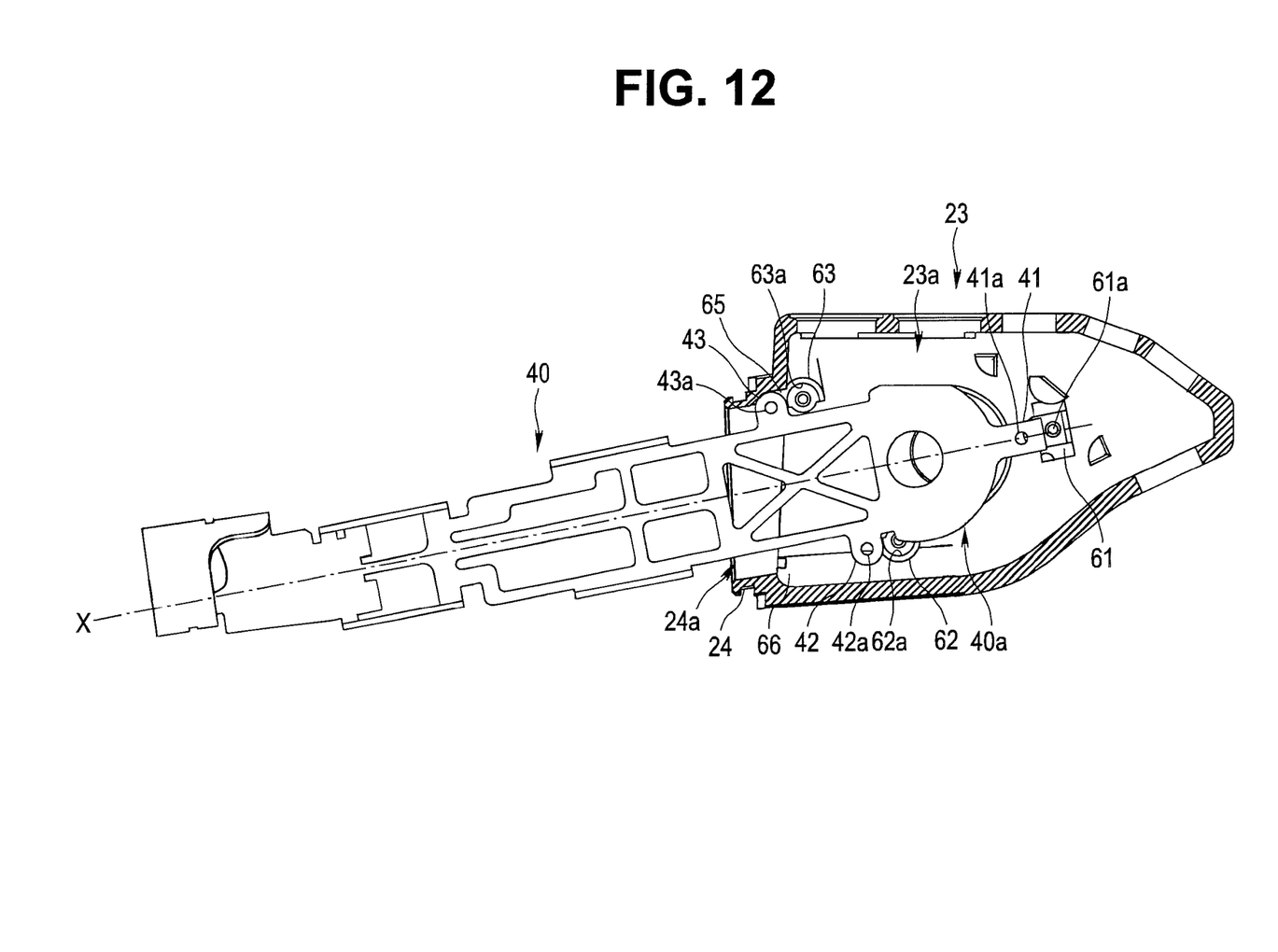
FIG. 12 illustrates the state where the frame member is inserted into the operation portion main body, according to the one aspect.

Then, as shown in FIGS. 11 and 12, the frame member 40 is moved obliquely while rotationally moving the direction of the longitudinal axis X of the frame member 40 along the plane (in parallel with the plate surface), to thereby allow the one end part 40a of the frame member 40 to be inserted into the operation portion main body 23 such that the second and third screw fixing portion 42, 43 can be passed through the opening portion 24a.

In addition, when the one end part 40a of the frame member 40 is passed through the opening portion 24a of the coupling portion 24, the second screw fixing portion 42 of the frame member 40 is brought close to the one concave-shaped portion 66 formed in the operation portion main body 23, as shown in FIG. 11. This enables the third screw fixing portion 43 to easily pass through the opening portion 24a of the coupling portion 24. Furthermore, the third screw fixing portion 43 is brought into a state close to the other concave-shaped portion 65 formed in the operation portion main body 23, and the one end part 40a of the frame member 40 is inserted into the operation portion main body 23. This allows the frame member 40, which is inserted into the opening portion 24a obliquely in the diagonal direction of the opening portion 24a, to be inserted into the operation portion main body 23 with the frame member 40 being in parallel with the long side direction of the opening portion 24a.

The frame member 40, the second and third screw fixing portions 42, 43 of which are inserted into the operation portion main body 23, is fixed to the operation portion main body 23 such that the first, second and third screw fixing portions 41, 42 and 43 are engaged with the concave portions 61a, 62a and 63a, respectively, to be fixed to the first, second and third screw receiving portions 61, 62 and 63 with the fixing screws 51 (see FIG. 2, FIG. 13 and FIG. 14).

As described above, with the endoscope operation portion structure according to the present embodiment, the second and third screw fixing portions 42, 43 are provided so as to protrude from the both side portions of the frame member 40, respectively, which enables a long distance between the screws of the second and third screw fixing portions 42, 43 to be ensured. Furthermore, the distance from the first screw fixing portion 41 to the second screw fixing portion 42 or the third screw fixing portion 43 also becomes longer. The three fixing screws 51 fix the frame member 40 to the operation portion main body 23 at apex positions of a big triangle. Therefore, the fixing strength is increased, to thereby enabling the frame member 40 to be stably fixed to the operation portion main body 23.

In addition, the first, second, and third screw fixing portions 41, 42 and 43 are engaged with the concave portions 61a, 62a and 63a of the first, second and third screw receiving portions 61, 62 and 63, and the surfaces in the thickness directions of the first, second and third screw fixing portions contact the wall surfaces which form the concave portions 61a, 62a and 63a to be held by the wall surfaces. This configuration restricts the movement of the frame member 40 in the insertion axis direction of the insertion portion 7, which is the longitudinal axis X, thereby preventing the frame member 40 from being misaligned.

The frame member 40 is thus configured such that the distances between the three positions fixed with the screws are longer than those in conventional configurations, which enables the frame member 40 to be stably fixed to the operation portion main body 23 without being misaligned, thereby preventing flexure of the frame member in the deflection direction due to stress generated at the insertion portion 7. That is, the increase in the fixing strength of the frame member 40 to the operation portion main body 23 prevents loosening of the frame member 40 in the deflection direction from occurring, thereby improving the durability of the frame member.

In addition, unlike the conventional configurations, even if the frame member 40 is not provided with a stopper for improving the fixing strength to the operation portion main body 23, the endoscope operation portion structure according to the present embodiment is capable of fixing the frame member 40 to the operation portion main body 23 by sufficient fixing strength, which reduces the number of components, and thereby assembling man-hours are also reduced. The endoscope operation portion structure thus configured provides advantages of reductions in initial cost, manufacturing cost and weight.

Note that, as shown in FIG. 6, the frame member 40 is configured such that a length L6 as the dimension between the apex A of the second screw fixing portion 42 and the apex B of the third screw fixing portion 43 in the width direction which is the direction perpendicular to the longitudinal axis X as the axis line direction of the insertion portion 7 is naturally set to be longer than the length L4 in the long side direction of the opening portion 24a of the coupling portion 24 of the operation portion main body 23 (L4<L6). Note that the length L6 is the maximum width of the frame member 40.

Therefore, as long as the length L6 is at least set to be longer than the length L4 in the long side direction of the opening portion 24a (L4<L6), the frame member 40 may be configured such that the respective lengths L1 and L2 in the width direction at the positions of the second and third screw fixing portions 42 and 43 of the frame member 40 are shorter than the length L4 in the long side direction of the opening portion 24a of the coupling portion 24 of the operation portion main body 23 (L4>L1, L2), for example.

The frame member 40, the length dimensions thereof are thus set, is moved such that the direction of the longitudinal axis X of the frame member is moved rotationally in parallel with the plate surface, as shown in FIGS. 9, 11 and 12, and furthermore, the frame member 40 is rotated so as to twist the plate surface, to be inclined in accordance with the diagonal direction of the opening portion 24a, thereby allowing the second and third screw fixing portions 42 and 43 to pass through the opening portion 24a and allowing the one end part 40a to be inserted into the operation portion main body 23, as shown in FIG. 10.

Then, similarly as described above, the frame member 40, the one end part 40a of which is inserted into the operation portion main body 23, is fixed to the operation portion main body 23 such that the first, second and third screw fixing portions 41, 42 and 43 are engaged with the concave portions 61a, 62a and 63a, respectively, to be fixed to the first, second and third screw receiving portions 61, 62 and 63, respectively, with the fixing screws 51. Also with the frame member 40 thus configured, the distances between the three positions fixed with the screws are longer than those in conventional configurations, which enables the frame member 40 to be stably fixed to the operation portion main body 23 without being misaligned, thereby preventing flexure in the deflection direction due to the stress generated at the insertion portion 7. Similarly as described above, increase in the fixing strength of the frame member 40 to the operation portion main body 23 prevents loosening of the frame member 40 in the deflection direction from occurring, thereby improving the durability of the frame member.

Regarding the configurations of the present invention as described above, the following cases can be considered.

Firstly, description will be made on the case where the length L4 in the long side direction of the opening portion 24a of the coupling portion 24 of the operation portion main body 23 is longer than the respective lengths L1 and L2 in the width direction at the positions of the second and third screw fixing portions 42, 43 of the frame member 40 (L4>L1, L2) and the length L4 is shorter than the length L6 which is the dimension between the apex A of the second screw fixing portion 42 and the apex B of the third screw fixing portion 43 in the width direction which is the direction perpendicular to the longitudinal axis X as the axis line direction of the insertion portion 7 (L4<L6).

In this case, the respective lengths L1 and L2 in the width direction at the positions of the second and third screw fixing portions 42 and 43 of the frame member 40 are shorter than the length L4 in the long side direction of the opening portion 24a of the coupling portion 24 of the operation portion main body 23, but longer than the length L6 which is the maximum width of the operation portion 24a. Therefore, when the frame member 40 is advanced straight toward the opening portion 24a, the second screw fixing portion 42 can pass through the opening portion 24a, but the third screw fixing portion 43 bumps against the coupling portion 24 and is unable to pass through the opening portion 24a. As a result, the one end part 40a of the frame member 40 cannot be inserted into the operation portion main body 23.

However, the frame member 40 includes the second and third screw fixing portions 42 and 43 provided so as to be shifted from each other in the direction of the longitudinal axis X. Therefore, the second screw fixing portion 42 is passed through the opening portion 24a, and thereafter the frame member 40 is advanced while being shifted or rotated along the frame plane, thereby enabling the third screw fixing portion 43 to pass through the opening portion 24a. As a result, the one end part 40a can be inserted in to the operation portion main body 23.

Next, description will be made on the case where the length L4 in the long side direction of the opening portion 24a of the coupling portion 24 of the operation portion main body 23 is shorter than the respective lengths L1 and L2 in the width direction at the positions of the second and third screw fixing portions 42, 43 of the frame member 40 (L4>L1, L2), and the length L5 in the diagonal direction of the opening portion 24a is longer than the length L6 as the dimension between the apex A of the second screw fixing portion 42 and the apex B of the third screw fixing portion 43 in the width direction which is the direction perpendicular to the longitudinal axis X as the axis line direction of the insertion portion 7 (L5>L6).

In this case, since the frame member 40 is configured such that the respective lengths L1 and L2 in the width direction at the positions of the second and third screw fixing portions 42 and 43 are longer than the length L4 in the long side direction of the opening portion 24a of the coupling portion 24 of the operation portion main body 23, neither the second screw fixing portion 42 nor the third screw fixing portion 43 can pass through the opening portion 24a only by shifting or rotating the frame member 40 along the plane thereof.

However, since the length L6 which is the maximum width of the frame member 40 is shorter than the length L5 in the diagonal direction of the opening portion 24a, if the frame member 40 is inclined and advanced straightforwardly, the second and third screw fixing portions 42, 43 can pass through the opening portion 24a, to thereby enable the one end part 40a to be inserted into the operation portion main body 23.

Finally, description will be made on the case where the length L4 in the long side direction of the opening portion 24a of the coupling portion 24 of the operation portion main body 23 is shorter than the respective lengths L1 and L2 in the width direction at the positions of the second and third screw fixing portions 42, 43 of the frame member 40 (L4<L1, L2), the length L5 in the diagonal direction of the opening portion 24a is shorter than the length L6 as the dimension between the apex A of the second screw fixing portion 42 and the apex B of the third screw fixing portion 43 in the width direction which is the direction perpendicular to the longitudinal axis X as the axis line direction of the insertion portion 7 (L5<L6), and the length L5 is longer than the lengths L1 and L2 (L5>L1, L2).

In this case, since the frame member 40 is configured such that the respective lengths L1 and L2 in the width direction at the positions of the second and third screw fixing portions 42, 43 is longer than the length L4 in the long side direction of the opening portion 24a of the coupling portion 24 of the operation portion main body 23, neither the second screw fixing portion 42 nor the third screw fixing portion 43 can pass through the opening portion 24a only by shifting or rotating the frame member 40 along the plane thereof. Furthermore, since the frame member 40 is configured such that the length L6 which is the maximum width of the frame member 40 is longer than the length L5 in the diagonal direction of the opening portion 24a, even if the frame member 40 is inclined, neither the second screw fixing portion 42 nor the third screw fixing portion 42 can pass through the opening portion 24a only by advancing the frame member straightforwardly.

However, the frame member 40 includes the second and third screw fixing portions 42, 43 provided so as to be shifted from each other in the direction of the longitudinal axis X. Therefore, the frame member 40 is inclined and the second screw fixing portion 42 is passed through the opening portion 24a first, and thereafter the frame member 40 is advanced while being shifted or rotated along the frame plane, thereby enabling the third screw fixing portion 43 to pass through the opening portion 24a. As a result, the one end part 40a can be inserted into the operation portion main body 23.

Note that the invention recited in the above-described embodiment is not limited to the embodiment and modified examples thereof and various kinds of modifications are possible in the practical stage without departing from the gist of the invention. Furthermore, the above-described embodiment includes inventions at the various stages, and various kinds of invention can be extracted by appropriately combining a plurality of the disclosed constituent elements.

Even if some constituent elements are deleted from all of the constituent elements shown in the embodiment, for example, if the described problem can be solved and the described effects can be obtained, the configuration in which the constituent elements are deleted can be extracted as the invention.

What is claimed is:

1. An endoscope operation portion structure comprising:
an operation portion main body for operating an endoscope;
a rectangular opening portion which is open on the operation portion main body and which has a long side and a short side;
a frame member having a longitudinal axis, and configured to be inserted from the opening portion into the operation portion main body along a direction of the longitudinal axis and arranged inside the operation portion main body;
a first fixing portion for fixing the frame member to the operation portion main body, the first fixing portion being provided so as to protrude from one side portion of the frame member; and
a second fixing portion for fixing the frame member to the operation portion main body, the second fixing portion being provided so as to protrude from an other side portion of the frame member,
wherein the frame member has a first distance along a short axis which is orthogonal to the longitudinal axis at a part where the first fixing portion is provided, and a second distance along the short axis at a part where the second fixing portion is provided, the first and second distances are both larger than a length of the long side of the opening portion, the first and second distances are shorter than a length in a diagonal direction in which corner portions of the opening portion where the long side and the short side intersect are opposed to each other in the diagonal direction, and
wherein a third distance between the first fixing portion and the second fixing portion in a direction along the short axis of the frame member is larger than the length of the diagonal direction of the opening portion, and the first fixing portion and the second fixing portion are respectively arranged at positions separated from each other by a predetermined distance in the longitudinal axis direction of the frame member.

2. The endoscope operation portion structure according to claim 1, wherein a third direction between the first fixing portion and the second fixing portion in the direction along the short axis of the frame member is shorter than the length in the diagonal direction of the opening portion.

3. The endoscope operation portion structure according to claim 1, further comprising a plurality of screw receiving portions to which the first fixing portion and the second fixing portion are fixed, the plurality of screw receiving portions being provided in the operation portion main body.

4. The endoscope operation portion structure according to claim 1, wherein the first fixing portion and the second fixing portion are formed as protrusions.

5. The endoscope operation portion structure according to claim 3, wherein the plurality of screw receiving portions include concave portions with which the first fixing portion and the second fixing portion are engaged such that side surfaces in thickness directions of the first fixing portion and the second fixing portion contact the concave portions.

* * * * *